US010497076B2

(12) United States Patent
Darguesse et al.

(10) Patent No.: US 10,497,076 B2
(45) Date of Patent: Dec. 3, 2019

(54) DEVICE, SYSTEM AND METHOD FOR PROVIDING CONTEXTUALIZED MEDICAL DATA

(75) Inventors: Frédéric Darguesse, Paris (FR); Mark Morwood, Bedford, MA (US); Brian McAlpine, Windham, NH (US)

(73) Assignee: CAPSULE TECHNOLOGIE, Andover, MA (US)

( * ) Notice: Subject to any disclaimer, the term of this patent is extended or adjusted under 35 U.S.C. 154(b) by 0 days.

(21) Appl. No.: 13/063,678

(22) PCT Filed: Sep. 8, 2009

(86) PCT No.: PCT/EP2009/061651

§ 371 (c)(1), (2), (4) Date: Mar. 11, 2011

(87) PCT Pub. No.: WO2010/029086

PCT Pub. Date: Mar. 18, 2010

(65) Prior Publication Data

US 2011/0202371 A1 Aug. 18, 2011

Related U.S. Application Data

(60) Provisional application No. 61/096,611, filed on Sep. 12, 2008.

(51) Int. Cl.

*G06Q 50/24* (2012.01)
*G16H 40/20* (2018.01)
*G16H 10/60* (2018.01)

(52) U.S. Cl.

CPC ............. *G06Q 50/24* (2013.01); *G16H 40/20* (2018.01); *G16H 10/60* (2018.01)

(58) Field of Classification Search

None

See application file for complete search history.

(56) References Cited

U.S. PATENT DOCUMENTS 6,283,761 B1 * 9/2001 Joao .............................. 434/236
7,154,397 B2 12/2006 Zerhusen et al.
(Continued)

FOREIGN PATENT DOCUMENTS

WO WO-2004/084720 10/2004
WO WO-2007/065015 6/2007
(Continued)

OTHER PUBLICATIONS

International Preliminary Report on Patentability for PCT/EP2009/061651 dated Mar. 15, 2011.
(Continued)

*Primary Examiner* — Michael Tomaszewski
(74) *Attorney, Agent, or Firm* — The Marbury Law Group, PLLC

(57) ABSTRACT

The invention concerns a point of care device comprising: a medical device connectivity module comprising connection means for collecting and storing medical data originating from at least one medical apparatus and data translation means for translating the received medical data into a common format; a proximity detection module comprising a reader and processing means for associating the point of care device with items within a range of the reader and generating association data relative to the association of the point of care device with the items; an interface module comprising processing means for merging the medical data in the common format with the generated association data so as to provide contextualized medical data, and sending means for sending said contextualized medical data to a contextual information server.

24 Claims, 1 Drawing Sheet

(56) References Cited

U.S. PATENT DOCUMENTS

| | | | | |
|---|---|---|---|---|
| 7,438,216 | B2 * | 10/2008 | Ambekar et al. | 235/375 |
| 8,036,925 | B2 * | 10/2011 | Choubey | 705/7.12 |
| 2004/0078219 | A1 * | 4/2004 | Kaylor | G06F 19/3418 705/2 |
| 2005/0209886 | A1 * | 9/2005 | Corkern | 705/2 |
| 2005/0242928 | A1 * | 11/2005 | Kirkeby | 340/286.07 |
| 2006/0036472 | A1 * | 2/2006 | Crockett | 705/3 |
| 2006/0089858 | A1 * | 4/2006 | Ling | 705/2 |
| 2006/0122863 | A1 * | 6/2006 | Gottesman et al. | 705/2 |
| 2006/0259326 | A1 * | 11/2006 | Ambekar | G06Q 50/22 705/2 |
| 2007/0033068 | A1 * | 2/2007 | Rao | A63B 24/00 705/2 |
| 2008/0004904 | A1 * | 1/2008 | Tran | 705/2 |
| 2009/0063193 | A1 * | 3/2009 | Barton et al. | 705/3 |
| 2009/0069642 | A1 * | 3/2009 | Gao et al. | 600/300 |
| 2009/0206992 | A1 * | 8/2009 | Giobbi et al. | 340/5.74 |
| 2010/0169120 | A1 * | 7/2010 | Herbst | G06Q 50/24 705/3 |
| 2011/0202371 | A1 * | 8/2011 | Darguesse et al. | 705/3 |
| 2012/0072238 | A1 * | 3/2012 | Collins, Jr. | G06F 19/3418 705/3 |

FOREIGN PATENT DOCUMENTS

| | | | | |
|---|---|---|---|---|
| WO | WO 2007065015 | A2 * | 6/2007 | |
| WO | WO-2008/033970 | | 3/2008 | |
| WO | WO 2008033970 | A2 * | 3/2008 | G06F 19/327 |
| WO | WO-2008033970 | A2 * | 3/2008 | G06Q 10/06 |
| WO | WO-2008/056033 | | 5/2008 | |
| WO | WO 2008056033 | A1 * | 5/2008 | G06F 19/327 |
| WO | WO-2008056033 | A1 * | 5/2008 | G06Q 10/06 |

OTHER PUBLICATIONS

International Search Report for PCT/EP2009/061651 dated Nov. 27, 2009.

* cited by examiner

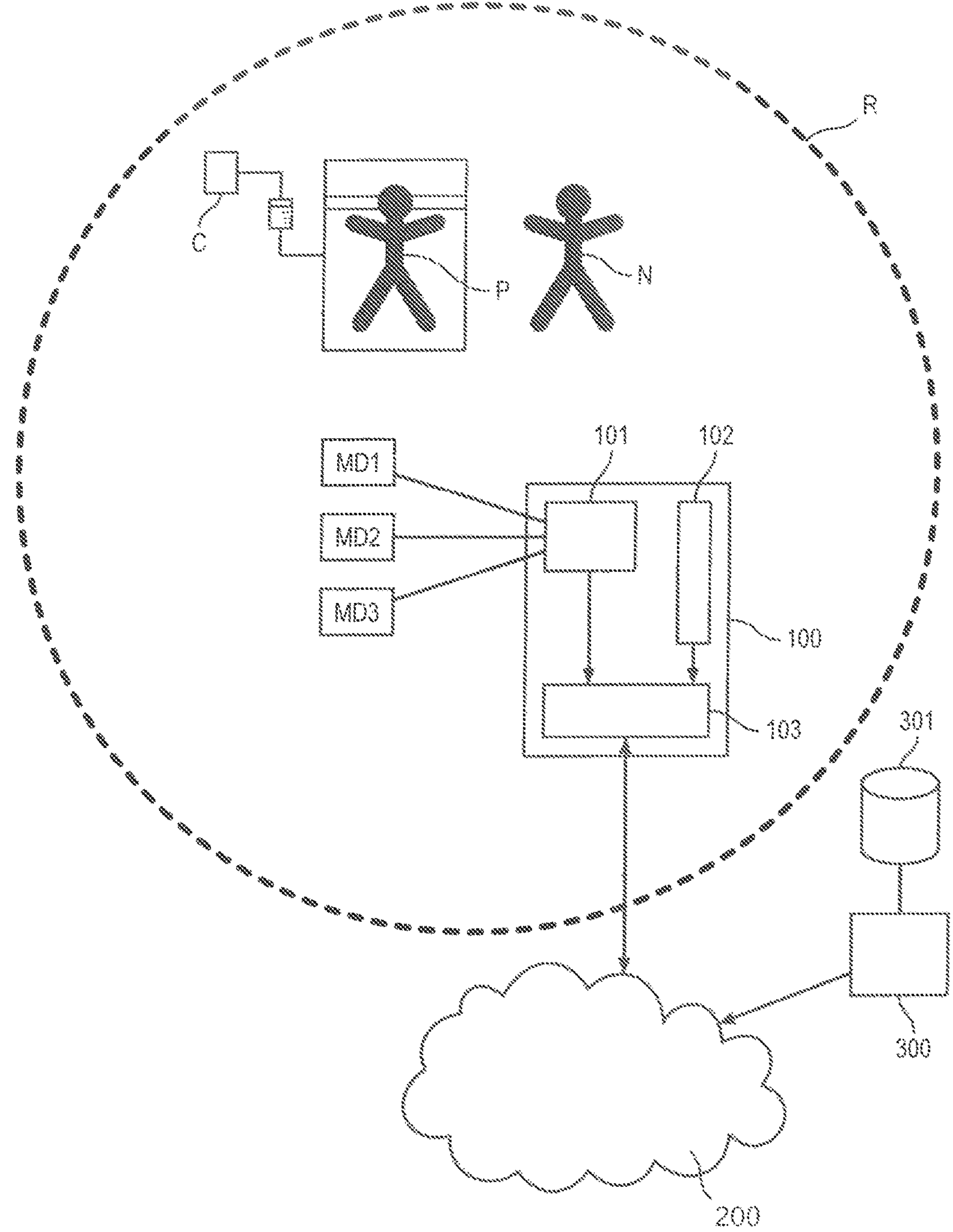
R
C
P
N
101
102
MD1
MD2
MD3
100
103
301
300
200

DEVICE, SYSTEM AND METHOD FOR PROVIDING CONTEXTUALIZED MEDICAL DATA

TECHNICAL FIELD

The invention relates to point of care devices, systems and processes, and more particularly to such devices, systems and processes that automatically detect and associate device encounters with items in a healthcare environment and that merge data resulting from this association with medical data originating from medical devices so as to provide contextualised medical data from which improved quality reports can be completed.

BACKGROUND ART

Clinicians in acute care settings always have a certain awareness or "context" about the patients they care for. For example—clinicians know who their patients are, why their patients have been admitted into the hospital, what medications their patients are taking, who the other responsible caregivers are, what rooms and beds their patient are in, and the current vital signs and lab results for their patients.

All of the following are considered examples of contextual-care data elements usually necessary for clinicians to provide safe and effective patient care.

Patient ID
Location (room/bed)
Diagnosis
Results
Current vital signs
Medications list
Allergies When clinicians interact with a specific patient (for example when they perform a task or procedure) they require additional "patient-centric" context in order to ensure accuracy and patient safety. As an example—when administering a medication, a nurse requires context in order to determine—is this the right patient, is this the correct dose for this patient, is there an order for this medication for this specific patient, is the patient allergic to this medication, etc.

There are two critical elements related to patient context and contextual care that must be considered:

Process Automation and Clinical Workflow—the specific work processes that are performed at the patient's bedside must be safe, as efficient as possible, and able to obtain all relevant contextual information in real-time.

Enterprise Application Enablement—In order for enterprise applications to be enabled to consume patient-specific point of care information, there must be an efficient process established and implemented to ensure the proper patient context is created and maintained for the medical devices that produce the patient information (i.e. vital signs data, alarms, device status information). Most medical devices in use today have no context about which patient they are connected to, which location (room/bed) the patient is located, or which caregiver is present at a given time (such as when a caregiver is performing a task or procedure).

In order to improve health management, information systems have been developed so as to manage the administrative, financial and clinical aspects of a hospital. In this respect, two information systems are generally interconnected: a Clinical Information System (CIS) which concentrates on patient-related and clinical-state-related data, and a Hospital Information System (HIS) which keeps track of related clinical and administrative issues.

There is currently an increase demand for improvements in patient point of care so as to avoid errors such as patient misidentification, wrong medication and false medication administration recording.

As for instance discussed in the paper "Positive Patient Identification using RFID and Wireless Networks" by Aguilar, der Putten and Maguire (Health Informatics Society of Ireland, 11th Annual Conference and Scientific Symposium, Dublin, Ireland, November 2006), various patient identification methods in hospitals have been proposed in order to improve upon current safety procedures. In particular, a handheld-based patient identification system has been proposed wherein each patient is given a RFID wristband and the clinician (nurse for instance) uses a RFID reader to read the patient's wristband and identify the patient.

Still making use of RFID technology, it has been proposed in US 2007/0267475 to implement a per-patient device that automatically detects and logs patient encounters with items (such as medical devices, drug containers, clinicians) with the benefit of not requiring that a clinician manually triggers a system to scan for or detect the item. The per-patient device may communicate with the Clinical Information Systems (CIS) so as to ascertain if a detected medical device, drug or the like has been approved or ordered for the patient.

SUMMARY OF THE INVENTION

It is an object of the invention to provide an improved device of this general type.

It is a further object of the invention to provide improved safety in patient point of care by offering quality reports derived from both medical data originating from the medical devices (such as infusion pumps, respirators, vital sign monitors, EEGs and the like) located in the point of care and data relating to patient encounters with items.

According to a first aspect of the invention, there is provided a point of care device according to the point of care device comprising:

a medical device connectivity module comprising connection means for collecting and storing medical data originating from at least one medical apparatus and data translation means for translating the received medical data into a common format;

a proximity detection module comprising a reader and processing means for associating the point of care device with items within a range of the reader and generating association data relative to the association of the point of care device with the items;

an interface module comprising processing means for merging the medical data in the common format with the generated association data so as to provide contextualized medical data, and sending means for sending said contextualized medical data to a contextual information server.

Preferred but non limitative features of this point of care device are as follows:

Point of care device, wherein an identification transmitter is attached to an item and wherein the reader is adapted to receive identification information from an identification transmitter within the range, said identification information uniquely identifying the item, Point of care device, wherein the identification transmitter is an RFID tag and the reader is an RFID reader, Point of care device, wherein the contextual information server has a database storing item information and wherein the processing means of the proximity detection module are further programmed to interrogate the server once an item is detected within the range of the reader to obtain the item information stored in the database, Point of care device, further comprising a display and wherein the processing means of the proximity detection module are further programmed to display a prompt asking if the association should be confirmed, Point of care device, further comprising a display and wherein the processing means of the proximity detection module are further programmed to display an alarm when the association is prohibited by the item information, Point of care device, wherein the processing means of the proximity detection module are further programmed to check if the association can be confirmed by comparing the item information with the medical data collected by the medical device connectivity module.

Point of care device, wherein the connection means of the medical device connectivity module includes a plurality of drivers which each provides an access to a medical device outputting medical data in either a standard or a proprietary format, and the data translation means of the medical device connectivity module are configured to translate the medical data in either a standard or a proprietary format into the common format, Point of care device, wherein the data translation means of the medical device connectivity module are further configured to merge into a single stream the medical data in the common format originating from a plurality of medical devices.

According to a second aspect of the invention, there is provided a system for providing patient care at a point of care, comprising a point of care device, and a server to which the contextualized medical data are distributed, the server being in communication with a database which stores item information about items that are attached to identification transmitters.

According to a third aspect, there is provided a process for providing patient care comprising the steps of:

collecting medical data originating from the at least one medical apparatus and translating the received medical data into a common format.

automatically associating a reader with an item that corresponds to an identification transmitter within a range of the reader, and generating association data;

merging the medical data in the common format with the generated association data so as to provide contextualized medical data, and distributing the contextualized medical data to a server.

BRIEF DESCRIPTION OF THE DRAWINGS

Other features and advantages of the invention will be more fully understood by referring to the following Detailed Description of Specific Embodiments that are given for illustrative purposes, and are in now way limitative, in conjunction with the unique drawing of which FIG. 1 is a block diagram of the system according to one embodiment of the second aspect of the invention.

DETAILED DESCRIPTION OF SPECIFIC EMBODIMENTS

As shown on FIG. 1, a point of care device 100 according to the first aspect of the invention.

The point of care device is preferably portable and battery powered. Optionally, the point of care device can be coupled to a docking station, for instance attached to a bed or a wall, connected to a power source. The docking station can further be connected to a computer network, for instance via a network cable or via an embedded wireless communication module.

The point of care device 100 includes a medical device connectivity module 101 comprising connection means for collecting medical data originating from at least one bedside medical apparatus MD1, MD2, MD3 and data translation means for translating the received medical data into a common format.

The connection means of the medical device connectivity module 101 can include a plurality of drivers which each provides an access to a medical device MD1-MD3 outputting medical data in either a standard or a proprietary format.

The connection means can therefore collect in real-time the medical data originating from the different medical devices MD1-MD3.

The point of care device 100 includes communication ports, typically serial communication ports, by which the device 100 can received medical data from the medical devices MD1-MD3.

The link with the device 100 is either wired or wireless (for instance according to the low power Zigbee protocol).

The data translation means of the medical device connectivity module 101 are configured to translate the medical data in either a standard or a proprietary format into the common format, for instance an industry-standard standard such as XML or HL7.

When several medical devices MD1-MD3 are connected to the point of care device 100, the data translation means of the medical device connectivity module 101 are further configured to merge into a single stream the medical data in the common format originating from the plurality of medical devices.

As a preferred embodiment, the medical device connectivity module 101 is implemented according to the DataCaptor™Connectivity Suite proposed by CapsuleTech, Inc.

The point of care device 100 further includes a proximity detection module 102 comprising a reader and processing means for associating the point of care device with items within a range R of the reader and generating association data relative to the association of the point of care device with the items.

As used in this description, the term item designates a thing to which a transmitter or a transponder (such as a RFID tag) can be attached, such as patient P or a thing that may come close to the point of care device. Exemplary items include medical devices MD1-MD3 used in care units (infusion pumps, medical monitors such as heart rate monitor), a drug container C, a surgical or procedural (i.e. endoscope) instrument, medical and surgical supplies, medications, a blood or milk bag, an implant, a bed, a wall or door or ceiling within a medical room, a clinician (such as a nurse N, or a therapist), a visitor.

As it will be understood by the following discussion, the association capabilities are based on the concept of associating items relative to a confirmed patient ID. The patient ID is indeed one of the 'items'—but the key point is that items are associated with a specific patient as opposed to the point of care device itself. Items are no really associated to the point of care device—this device is used to facilitate and establish the actual associations.

More particularly, an identification transmitter is attached to an item and stores identification information which uniquely identifies the item.

The reader is adapted to receive identification information from the identification transmitter when said transmitter is within the range R of the reader, so as to uniquely detect the presence of the item within the range.

The reader uses an antenna to emit the radiofrequency necessary to active the identification transmitters. The antenna design, the frequency of the beacon sent by the reader and the energy level used are developed to ensure proper coverage of any typical hospital room (containing objects that create interference like the bed) while limiting the radiation level to the minimum.

According to a preferred embodiment, the identification transmitter is an RFID tag (either passive or active) and the reader is an RFID reader.

Anyhow, the invention is not limited to RFID technology, and other types of transmitters can be used, such as for instance a Bluetooth, Ultrasound, or a WiFi transmitter.

The processing means of the point of care device can further be configured so as to confirm association with an item (for instance by displaying an item related information on the point of care device's screen) in the range of the reader only after the item has been detected within the range for a period of time longer than a first pre-set delay. In the same manner, the processing means of the point of care device can be configured to confirm that an item is no longer associated (for instance by removing the item related information on the screen) only after it has been detected that the item is not within the range for a period of time longer than a second pre-set delay.

The processing means can further be configured so as to implement an aging algorithm for detected tags to avoid tags appearing and disappearing unexpectedly if radiofrequency interferences momentarily make tags unreadable. Once a tag becomes visible, the aging algorithm periodically checks for presence. If at some point the tag is not visible anymore, the tag age is updated to make the tag older. Once the tag reaches a certain age, it is considered as gone. The tag age limit is configurable to accommodate with different radiofrequency environments that can be more or less prone to interferences.

In use, such as in a hospital or other healthcare facility, a separate point-of-care device 100 is assigned to each patient. Alternatively, a separate point-of-care device 100 can be assigned to each room of the hospital.

The point of care device 100 can thus detect when an item (such as a patient P, a nurse N, a medical device MD1-MD3, a drug container C, a surgical instrument) is brought within the range of the reader. This is in particular the case when the point of care device 100 is fixed (for instance attached to a docking station in an Intensive-Care Unit room) and items are brought in range. This is also the case when the point of care device 100 is mobile (for instance removed from the docking station and carried by a nurse) and the point of care device is itself brought into range of items already in a room (for instance the med-surg room).

As a result the point of care device 100 can automatically associate itself with the items that are close to it.

Point of care devices can further communicate with each others (either through a computer network 200 and directly by means of their embedded wireless communication module) so as to avoid incorrect association of a point of care device with items that are within the range of the reader but that in reality are to be associated with another point of care device (as they are for instance located in another room.

The point of care device 100 further communicates via the communication network 200 with a server 300, typically a server hosted by a Clinical Information System (CIS).

The point of care device 100 may be connected with the computer network 200 either via a wireless or a wired link, or optionally via a docking station to which it is coupled.

The server 300 is in communication with a database 301 which stores item information about items that are attached to identification transmitters.

Item information relative to a patient may include its name, its medical file (actual prescription, known allergies), etc.

Item information relative to a nurse may include its name, the patients the nurse took care of or is to take care of, its timetable, etc.

Item information relative to a medical device may include its name, its type, its possible settings, the last time the device was cleaned or checked and the next time it has to be cleaned or checked, etc.

Item information relative to a drug container may include its designation.

The processing means of the proximity detection module 103 can further be programmed to interrogate the server 300 once an item is detected within the range R of the reader to obtain the item information stored in the database 301.

In a preferred embodiment, the point of care device 100 comprises a display such a touch-sensitive screen.

In an embodiment, the processing means of the proximity detection module 101 are programmed to display a prompt asking if the association should be confirmed. In this respect, item information retrieved from the database can be displayed so that a nurse can confirm that the association is correct. For instance the nurse can confirm via the touch-sensitive screen that a specific drug bag has been brought close to the device 100 for administration of the drug to the patient and therefore confirm the association {point of care device+patient+drug bag}. The nurse can also visualize on the display the dosage that has been prescribed to the patient (item information relative to the patient), and visually check that the drug bag is set to the correct dosage.

In another embodiment, the processing means of the proximity detection module 11 are programmed to display an alarm when the association is prohibited by the item information. For instance, a drug bag has been brought for administration to the patient but the item information relative to the patient indicates that the patient is allergic to this drug. An alarm is thus displayed to alert the nurse that the association {patient+drug bag} should not be performed.

In yet another embodiment, the processing means of the proximity detection module 101 are programmed to check if the association can be confirmed by comparing the item information with the medical data collected by the medical device connectivity module 102. For instance, the item information relative to the patient indicates that particular dosage for drug is prescribed and the medical device connectivity module 102 collects medical data originating from an infusion pump delivering said drug. The medical device connectivity module 102 can in particular retrieve the actual settings of the infusion pump, so that a comparison can be performed between the actual settings and the prescribed dosage.

The point of care device 100 further comprises an interface module 103 comprising processing means for merging the medical data in the common format (generated by medical device connectivity module 101) with the association data (generated by the proximity detection module 102) so as to provide contextualized medical data.

The interface module 103 further comprises sending means for distributing the contextualized medical data to the server 300.

In a particular embodiment, the interface module can also be configured so that the contextualized medical data can be shared with other external systems, thus providing device-to-device interoperability. For instance, the contextualized medical data can be provided to one of the medical devices MD1-MD3 from which the point of care device 100 receives medical data, or even a medical device from which medical data are not pulled from (contextualized medical data are thus sent to this medical device, while medical data elaborated by this device are not received by the point of care device 100). Device-to-device interoperability can also be established in between the point of care device 100 and communication devices (such as cell phones, PDA, pagers, etc.) carried by clinicians.

Within the framework of the invention, device-to-device interoperability can be safely and effectively performed and maintained as patient ID and device contexts are properly established and continuously coordinated at the patient's bedside.

Device-to-device interoperability can for instance be provided so as to share with a patient-controlled analgesia (PCA) pump contextualized medical data embedding medical data originating from a cardiac monitor. Upon gaining knowledge that the patient presents a respiratory problem, the PCA pump takes a medical decision, such as stopping the delivery of analgesia.

Information relating to the patient can be pushed to a medical device so as to provide for additional security check. For instance, the weight of a patient can be sent to an infusion pump, so that it can be checked that the set dose is compatible with the patient's weight.

Another example of device-to-device interoperability is the pushing of alarms to the communication devices (such as cell phones, PDA, pagers, etc.) carried by clinicians. For instance an alarm relating to a cardiac arrest can be pushed to a given nurse that has to acknowledge receipt of the alarm. If no acknowledgement is received within a set delay, the alarm can be pushed to other clinicians, for instance with several escalation levels. In particular, the point of care device 100 knows which nurse was recently within range, and can therefore push the alarm to this particular nurse.

The point of care device 100 according to the first aspect of the invention is configured to distribute to the server 300, as well as to other devices as seen above in relation to device-to-device interoperability, real-time medical data (translated in a common format) along with the context within which these data have been collected. By context, it is meant the detected association between the point of care device 100 and the various items within the range of the reader.

Medical data from medical devices MD1-MD3 comprise state data (such as physiological parameters of the patient), treatment data (such as the device settings or mode) and situation data (such as alarms or alerts generated by the medical device.

If connection is lost with Server 300 (for instance when the point of care device making use of wireless communication is mobile and brought out of range of the wireless network), the point of care device 100 can store data from medical devices MD1-MD3 for a few hours, for instance between 4 and 6 hours, until the connection with Server 300 is available again.

Real-time Medical data originating from medical devices MD1-MD3 are time-stamped by the point of care device 100 and are stored in a buffer when connection is lost. When connection with the server is available again, stored data are pushed to the server, while incoming medical data are blocked until data recovery is over. In a variant, the server indicates that it is available again and allocates bandwidth for data recovery.

The medical data are contextualized by merging with the association data derived from proximity detection of for instance the patient, its location (when the tag is present within the medical room), the clinician that takes care of the patient, the instruments, bags and containers that are used, etc.

As presented above, data from several medical devices are translated in a common format and merged with association data in a single stream, such as an XML or HL7 stream. This common format is then contextualized by the point of care device with the patient identification information. The point of care device then sends the contextualized medical device data to a central server that aggregates contextualized data from several point of care devices to provide a contextualized medical data feed to the applications consuming this feed, like the EMR.

The contextualised medical data notably allow for an improved routing of alarms and alerts. Consider for instance that a medical device associated with the patient generates an alarm or alert (typical examples are an infusion pump sending an "near of infusion end" alert or a heart rate monitor sends an alarm), the contextualized medical data transmitted to the server will push this alarm/alert along with information about the nurse that took care of or is currently in proximity of a specific patient. This particular nurse can then be contacted by the CIS so as to visit the patient. Alternatively a nurse identified as being currently close to the patient's room may be contacted.

In addition to alarms and alerts, new clinical data can be derived from the contextualized medical data. For instance, a new clinical indicator (such as a probability of a cardiac arrest) can be elaborated by merging or analysing medical data originating from several medical devices along with demographic data of the patient. This new clinical indicator can further be sent to a medical device where it is to be used as a new clinical data input.

The contextualized medical data also allows for automated verification of medical order execution. The contextualized medical data indeed allows checking that a prescribed medical device or drug bag has been associated with the patient, that the prescribed medical device associated with the patient is active (via the collection of medical data), that the prescribed drug has been administrated, etc. Furthermore, once order execution is confirmed, patient can be billed taking into account all the items that were associated to him during its stay in the hospital.

More generally, clinicians have a critical requirement to perform various associations or assignments (i.e. contextual mappings) to facilitate the process of care and provide a level of safety. Clinicians also have a need to acquire real-time information from many disparate medical devices and systems found at the point-of-care. This real-time information that needs to be captured from these devices and systems is critical for the management of the patient's process of care and for timely decision making in the event of a life threatening condition. There are several critical point-of-care (POC) nursing workflow processes (and relevant applications) related to Patient ID and patient-context that are necessary and which can be performed by a Point of care device including:

Patient ID to associate and automate data to EMR—Data parameters from POC medical devices need to be assigned to the "right patient" record for nursing documentation purposes (e.g. in a CIS/HIS nursing documentation module). The patient-context (association) process that a nurse must perform and which can be automatically performed by a point of care device is linking the patient ID to a specific medical device ID.

Patient ID to associate and automate alarm/alert management—Medical devices need to be assigned to the "right patient" at the POC to enable alarms/alerts to be sent to clinicians who typically carry a communications device (phone, pager, PDA, etc.). This integration typically includes patient connected medical devices and systems that generate critical alerts such as nurse call systems. The patient-context process that a nurse must perform and which can be automatically performed by a point of care device is linking the patient ID to various medical device ID's and then linking their caregiver ID to a handheld communication device ID or PIN number.

Patient ID to automate the medication administration process—This process is where the nurse administers "the five rights of medication administration" which verifies the right patient, right drug, right dose, right route, and right time. The patient-context process that a nurse must perform and which can be automatically performed by a point of care device is linking the patient ID to a patient-specific medication ID, linking the medical device ID to the patient ID for infused drugs, and linking their caregiver ID to the patient ID.

Patient ID to automate specimen collection—Specimens include breast milk verification, blood draws, urine samples, and blood transfusions. The patient-context process that a nurse must perform and which can be automatically performed by a point of care device is linking the patient ID to the specimen to ensure patient safety.

The invention claimed is:

1. A point of care device, comprising:

a memory;

a display;

a medical device communication port;

a reader configured to receive item identification information originating from at least one item;

a processor coupled to the memory, display, medical device communication port, and the reader, configured with processor-executable instructions to perform operations comprising:

receiving a patient ID from a patient transmitter;

associating the point of care device with the patient ID when it is determine that the point of care device is within range of the patient transmitter for a period of time longer than a first pre-set delay;

determining whether the at least one item is within range of the reader for a period of time longer than the first pre-set delay;

associating the at least one item with the point of care device that is associated with the patient in response to determining that the at least one item is within the range of the reader for the period of time longer than the first pre-set delay;

generating association data in response to associating the at least one item with the point of care device that is associated with the patient ID;

receiving, via the medical device communication port, medical data originating from at least one medical device including at least one of an infusion pump, a respirator, a vital sign monitor, or an EEG;

generating contextualized medical data based on the medical data and the association data, wherein the contextualized medical data provides information regarding context of the medical data with respect to the patient ID;

transmitting, via a communication network, the contextualized medical data to a server having a database storing item information; and transmitting, via the medical device communication port, the contextualized medical data to the at least one medical device to cause the at least one medical device to adjust one or more settings based on the received contextualized medical data.

2. The point of care device of claim 1, wherein the reader is an RFID reader.

3. The point of care device of claim 1, wherein the processor is further configured with processor-executable instructions to perform operations comprising:

determining whether the received item information is prohibited from use with the patient based on the contextualized medical data.

4. The point of care device of claim 1, wherein the processor is further configured with processor-executable instructions to perform operations comprising:

confirming whether the received item information is authorized for use with the patient based on the contextualized medical data.

5. The point of care device of claim 3, wherein the processor is further configured with processor-executable instructions to perform operations comprising:

displaying a prohibition alert in response to determining that the received item information is prohibited from use with the patient based on the contextualized medical data.

6. The point of care device of claim 4, wherein the processor is further configured with processor-executable instructions to perform operations comprising:

displaying a confirmation alert in response to determining that the received item information is authorized for use with the patient based on the contextualized medical data.

7. The point of care device of claim 1, wherein the processor is further configured with processor-executable instructions to perform operations comprising:

disassociating the point of care device with the at least one item if the at least one item is not located within the range for a second period of time longer than a second pre-set delay.

8. The point of care device of claim 1, wherein the processor is further configured with processor-executable instructions to perform operations comprising:

disassociating the point of care device with the patient if the patient is not located within the range for a second period of time longer than a second pre-set delay.

9. The point of care device of claim 1, wherein the processor is further configured with processor-executable instructions to perform operations such that receiving the identification information from the item causes the processor to perform operations such that associating the at least one item with the point of care device that is associated with the patient is in response to determining that the item is not already associated with a different point of care device.

10. The point of care device of claim 1, wherein the processor is further configured with processor-executable instructions to perform operations comprising:

translating the medical data from the at least one medical device into a common format; and storing a result of translating the medical data into the common format in the memory.

11. A method of providing patient care, comprising receiving a patient ID from a patient transmitter;

receiving, by a medical device communication port of a point of care device, medical data originating from at least one medical device including at least one of an infusion pump, a respirator, a vital sign monitor, or an EEG;

receiving, by a reader of the point of care device, item identification information originating from at least one item;

associating, by a processor of the point of care device, the point of care device with the patient ID when it is determined that the point of care device is within range of the patient transmitter for a period of time longer than a first pre-set delay;

determining, by the processor, whether the at least one item is within range of the reader for a period of time longer than the first pre-set delay;

associating, by the processor, the at least one item with the point of care device that is associated with the patient in response to determining that the at least one item is within the range of the reader for the period of time longer than the first pre-set delay;

generating, by the processor, association data in response to associating the at least one item with the point of care device that is associated with the patient;

generating contextualized medical data based on the medical data and the association data, wherein the contextualized medical data provides information regarding context of the medical data with respect to the patient ID;

transmitting, via a communication network, the contextualized medical data to a server having a database storing item information; and transmitting, via the medical device communication port, the contextualized medical data to the at least one medical device to cause the at least one medical device to adjust one or more settings based on the received contextualized medical data.

12. The method of claim 11, wherein the reader is an RFID reader.

13. The method of claim 11, further comprising:

determining whether the received item information is prohibited from use with the patient based on the contextualized medical data.

14. The method of claim 11, further comprising:

confirming whether the received item information is authorized for use with the patient based on the contextualized medical data.

15. The method of claim 13, further comprising:

displaying a prohibition alert in response to determining that the received item information is prohibited from use with the patient based on the contextualized medical data.

16. The method of claim 14, further comprising:

displaying a confirmation alert in response to determining that the received item information is authorized for use with the patient based on contextualized medical data.

17. The method of claim 11, further comprising:

disassociating the point of care device with the at least one item if the at least one item is not located within the range for a second period of time longer than a second pre-set delay.

18. The point of care device of claim 11, further comprising:

disassociating the point of care device with the patient if the patient is not located within the range for a second period of time longer than a second pre-set delay.

19. The method of claim 11, wherein associating the at least one item with the point of care device that is associated with the patient is in response to determining that the item is not already associated with a different point of care device.

20. The method of claim 11, further comprising:

translating the medical data from the at least one medical device into a common format; and storing a result of translating the medical data into the common format in the memory.

21. A method of customizing settings of a medical device including one of an infusion pump, a respirator, a vital sign monitor, or an EEG, comprising:

transmitting medical data medical device settings information to a point of care device that is within range of the point of care device;

generating medical data;

transmitting the generated medical data to the point of care device;

receiving contextualized medial information generated by the point of care device based on the transmitted medical data and association data, wherein the association data associates the medical device with a patient ID and the point of care device; and updating one or more settings based on the received contextualized medical information.

22. The point of care device of claim 1, wherein causing the at least one medical device to modify one or more settings, comprises:

modifying, by an infusion pump, a medication dosage being delivered to the patient based on the received contextualized medical data.

23. The method of claim 11, wherein causing the at least one medical device to modify one or more settings, comprises:

modifying, by an infusion pump, a medication dosage being delivered to the patient based on the received contextualized medical data.

24. The method of claim 21, wherein updating one or more settings based on the received contextualized medical information, comprises:

modifying a medication dosage being delivered to the patient based on the received contextualized medical data.

* * * * *